(12) United States Patent
Smith

(10) Patent No.: US 8,968,341 B2
(45) Date of Patent: *Mar. 3, 2015

(54) WOUND CLOSURE DEVICE

(71) Applicant: Covidien LP, Mansfield, MA (US)

(72) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/886,715

(22) Filed: May 3, 2013

(65) Prior Publication Data

US 2013/0238000 A1    Sep. 12, 2013

Related U.S. Application Data

(63) Continuation of application No. 12/908,944, filed on Oct. 21, 2010, now Pat. No. 8,435,252.

(60) Provisional application No. 61/260,121, filed on Nov. 11, 2009.

(51) Int. Cl.
   *A61B 17/04*      (2006.01)
   *A61B 17/00*      (2006.01)
   *A61B 17/06*      (2006.01)

(52) U.S. Cl.
   CPC ......... *A61B 17/0482* (2013.01); *A61B 17/0057* (2013.01); *A61B 17/0483* (2013.01); *A61B 2017/00637* (2013.01); *A61B 2017/00663* (2013.01); *A61B 2017/0472* (2013.01); *A61B 2017/06042* (2013.01)
   USPC .......................................... 606/144; 606/148

(58) Field of Classification Search
   USPC .......................... 606/139, 144–145, 147–148; 289/16–17; 112/169
   See application file for complete search history.

(56) References Cited

U.S. PATENT DOCUMENTS

| | | | |
|---|---|---|---|
| 4,733,664 A | 3/1988 | Kirsch et al. | |
| 5,830,232 A * | 11/1998 | Hasson ........................ | 606/213 |
| 6,911,034 B2 | 6/2005 | Nobles et al. | |
| 7,160,309 B2 | 1/2007 | Voss | |
| 7,235,087 B2 | 6/2007 | Modesitt et al. | |
| 7,449,024 B2 | 11/2008 | Stafford | |
| 2004/0097982 A1 | 5/2004 | Jugenheimer et al. | |
| 2005/0043746 A1 | 2/2005 | Pollak et al. | |
| 2005/0149066 A1 | 7/2005 | Stafford | |
| 2005/0588707 | 12/2005 | De Canniere et al. | |
| 2006/0030868 A1 | 2/2006 | Bennett | |
| 2006/0069397 A1 | 3/2006 | Nobles et al. | |
| 2009/0143808 A1 | 6/2009 | Houser | |

* cited by examiner

*Primary Examiner* — Elizabeth Houston
*Assistant Examiner* — Robert Lynch

(57) ABSTRACT

A suturing device includes a housing having an elongated tubular member extending from a distal end thereof. A head assembly is disposed at a distal end of the elongated tubular member and is configured to retain a portion of a suture therein. At least one arm member is positioned adjacent the elongated tubular member. Each arm members includes a ferrule assembly disposed at a distal end thereof. Each ferrule assembly is positioned within a recess defined within the elongated tubular member and is configured to releasably retain a ferrule therein. Each ferrule is configured to retain a portion of the suture therein. Each arm member is rotatable to rotate the ferrule assembly disposed thereon between a first position, wherein the ferrule assembly is disposed within the recess, and a second position, wherein the ferrule assembly extends at least partially radially outwardly from the recess.

10 Claims, 3 Drawing Sheets

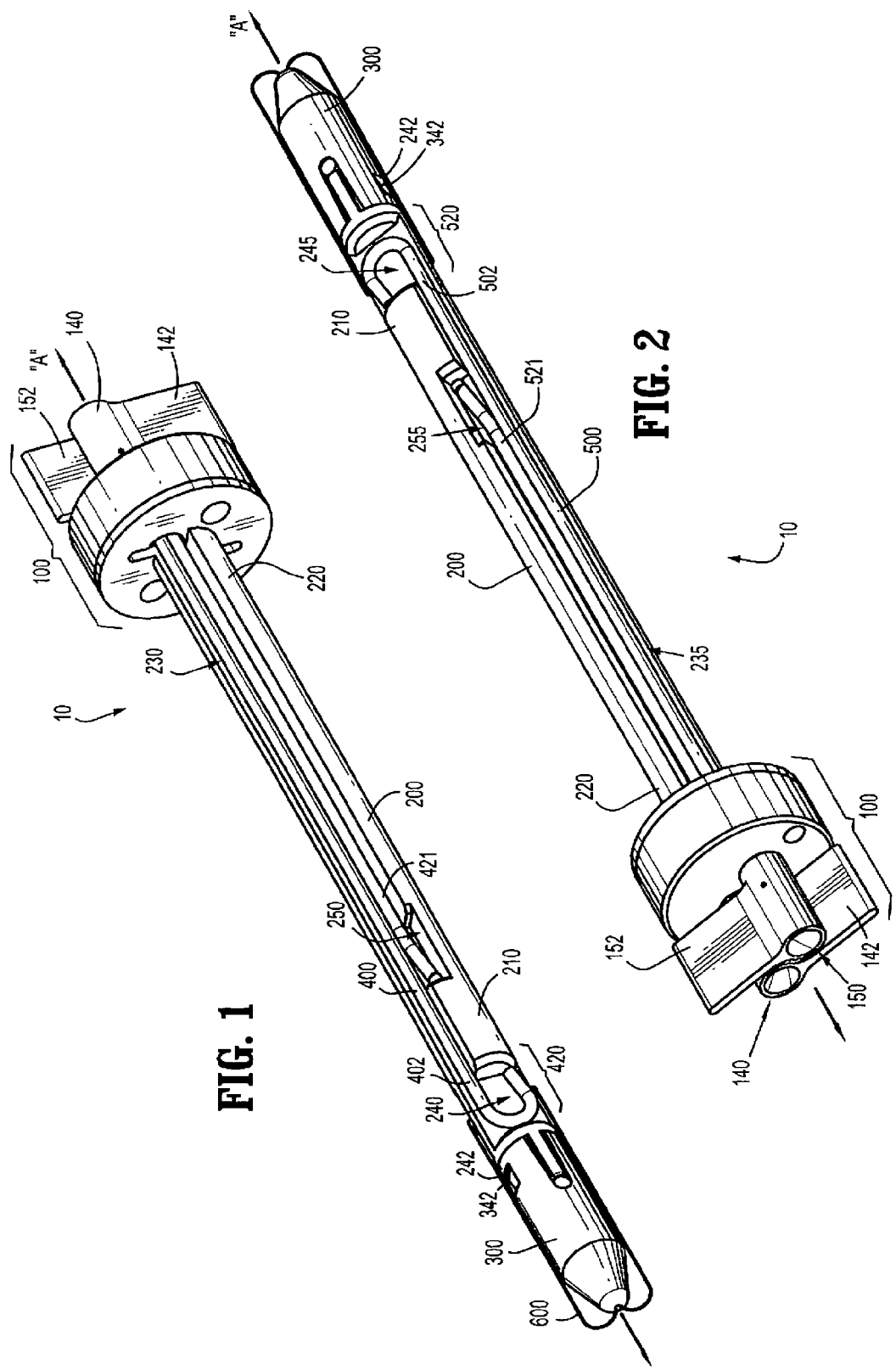

WOUND CLOSURE DEVICE

CROSS-REFERENCE TO RELATED APPLICATION

The present application is a continuation application of U.S. patent application Ser. No. 12/908,944 filed on Oct. 21, 2010, which claims the benefit of and priority to U.S. Provisional Application Ser. No. 61/260,121 filed on Nov. 11, 2009, the entire contents of each of which are incorporated by reference herein.

BACKGROUND

1. Technical Field

The present disclosure relates to a wound closure device and, more particularly, to a wound closure device for suturing an opening in tissue.

2. Background of Related Art

Puncture wounds, wounds that pierce through tissue, may result from trauma or may be intentionally created in order to provide access to a body cavity during surgical procedures. During endoscopic surgical procedures, for example, a trocar device is utilized to puncture the peritoneum to provide an access port by way of a cannula through the abdominal wall. Generally, a trocar and/or cannula is placed through the abdominal wall for introduction of surgical instrumentation which is necessary to carry out the surgical procedure. In this manner, the surgeon may introduce a surgical instrument such as a grasper, scissor, clip applier, stapler or any other surgical instrument which may be necessary during the particular surgical procedure. Once the procedure is complete, it is necessary to close the wound.

Conventional instruments for closing puncture wounds generally include a shaft that can be extended into the body through either the puncture wound itself (in the case of a puncture caused by trauma) or through a cannula (in the case of a puncture created to access a surgical site). Suture retaining needles are then deployed from the shaft into tissue. Unfortunately, the mechanisms used for deploying the needles are often cumbersome and may make the extension and/or retraction of the suturing device difficult.

In the prior art, U.S. Pat. No. 7,160,309 discloses a suturing device including a plurality of extendable projections configured to retain sutures thereon. Needles may then be passed through tissue to retrieve the sutures from the extendable protection. U.S. Pat. No. 7,235,087 discloses an articulating suturing device including a shaft having an articulated foot disposed at a distal end thereof. The foot includes suture attachment cuffs that lockingly engage needles such that the cuffs can be withdrawn upon withdrawal of the needles. U.S. Pat. No. 7,449,024 discloses a suturing device having at least two arms that are extendable from the shaft of the suturing device. The arms are rotated about a pivot to extend from the shaft. Needles may then be inserted into engagement with the arms to retrieve a suture from the arms. U.S. Patent Application Publication No. 2006/0069397 discloses a suturing apparatus similar to that of U.S. Pat. No. 7,449,024, discussed above, and further discloses a handle assembly for actuating the suturing apparatus.

SUMMARY

In accordance with the present disclosure, a suturing device is provided, the suturing device including a housing, a head assembly and one or more arm members. The housing includes an elongated tubular member extending from a distal end thereof. The head assembly is disposed at a distal end of the elongated tubular member and is configured to retain a portion of a suture therein. The arm member(s) is positioned adjacent the elongated tubular member and includes a ferrule assembly disposed at a distal end thereof. The ferrule assembly is positioned within a recess defined within the elongated tubular member and is configured to releasably retain a ferrule therein. The ferrule is configured to retain a portion of the suture therein. The arm member(s) is selectively rotatable to rotate the ferrule assembly disposed thereon between a first position, wherein the ferrule assembly is disposed within the recess, and a second position, wherein the ferrule assembly extends at least partially radially outwardly from the recess.

In one embodiment, the ferrule assembly includes a ferrule holder configured to releasably retain the ferrule therein.

In another embodiment, a guide tube extending distally from the housing and along each of the arm members is provided. Each guide tube is configured to permit translation of a needle therethrough and to direct the needle toward the ferrule retained within the ferrule assembly.

In yet another embodiment, the needle and the ferrule are dimensioned to engage each other in a male-female friction-fit engagement, although other configurations are contemplated.

In still another embodiment, the suturing device further includes a tissue clamp disposed about the elongated tubular member. The tissue clamp is configured to translate along the elongated tubular member to retain tissue in place during operation of the suturing device.

In still yet another embodiment, the housing further includes one or more rotatable flange extending proximally therefrom. The flanges configured to be selectively rotated to rotate the arm members and, thus, the ferrule assemblies, between the first and second positions.

Another embodiment of a suturing device provided in accordance with the present disclosure includes an elongated tubular member and one or more arm members positioned adjacent the elongated tubular member and extending therealong. The arm member(s) includes a ferrule assembly disposed at a distal end thereof that is initially disposed within a recess defined within the elongated tubular member. As in the previous embodiment, the ferrule assembly is configured to releasably retain a ferrule therein and is rotatable upon rotation of the arm member from a first position, wherein the ferrule assembly is disposed within the recess, and a second position, wherein the ferrule assembly extends at least partially radially outwardly from the recess. A guide lumen is coupled to and extends along each arm member. The guide member(s) is rotated about the arm member upon rotation of the arm member between the first and second positions such that, in the second position, the guide lumen directs a needle inserted therethrough toward the ferrule of the ferrule assembly.

The suturing instrument may further be configured according to any of the embodiments discussed above.

A method for suturing is also provided in accordance with the present disclosure. The method includes providing a suturing device according to any of the above embodiments. The method further includes inserting the suturing device into an opening in tissue such that the ferrule is positioned adjacent an internal face of tissue, rotating the ferrule assembly from the first position to the second position such that the ferrule assembly extends radially outwardly from the recess defined within the elongated tubular member, translating a needle distally through tissue and into engagement with ferrule, and translating the needle proximally through tissue such that the ferrule and the portion of suture are also translated through tissue.

In one embodiment, the method further includes removing the ferrule from the needle, translating the needle distally through tissue and into engagement with the ferrule retained within the ferrule assembly of a second arm member, translating the needle having the ferrule in engagement therewith proximally through tissue such that the suture is disposed through tissue, rotating the ferrule assemblies to the first position, removing the suturing device from the opening in tissue, and tying off the suture.

In embodiments where a guide tube is provided, the needle is inserted through the guide tube such that the needle is directed through tissue and toward the ferrule retained within the ferrule assembly.

In embodiments where a tissue clamp is provided, the tissue clamp is translated distally along the elongated tubular member to clamp tissue between the tissue clamp and ferrules before the needle is translated distally through tissue and into engagement with the ferrule.

BRIEF DESCRIPTION OF THE DRAWINGS

Various embodiments of the presently disclosed suturing instrument are described hereinbelow with references to the drawings, wherein:

FIG. 1 is a front, perspective view of a suturing device in accordance with the present disclosure;

FIG. 2 is a rear, perspective view of the suturing device of FIG. 1;

DETAILED DESCRIPTION OF THE EMBODIMENTS

Figure 3:
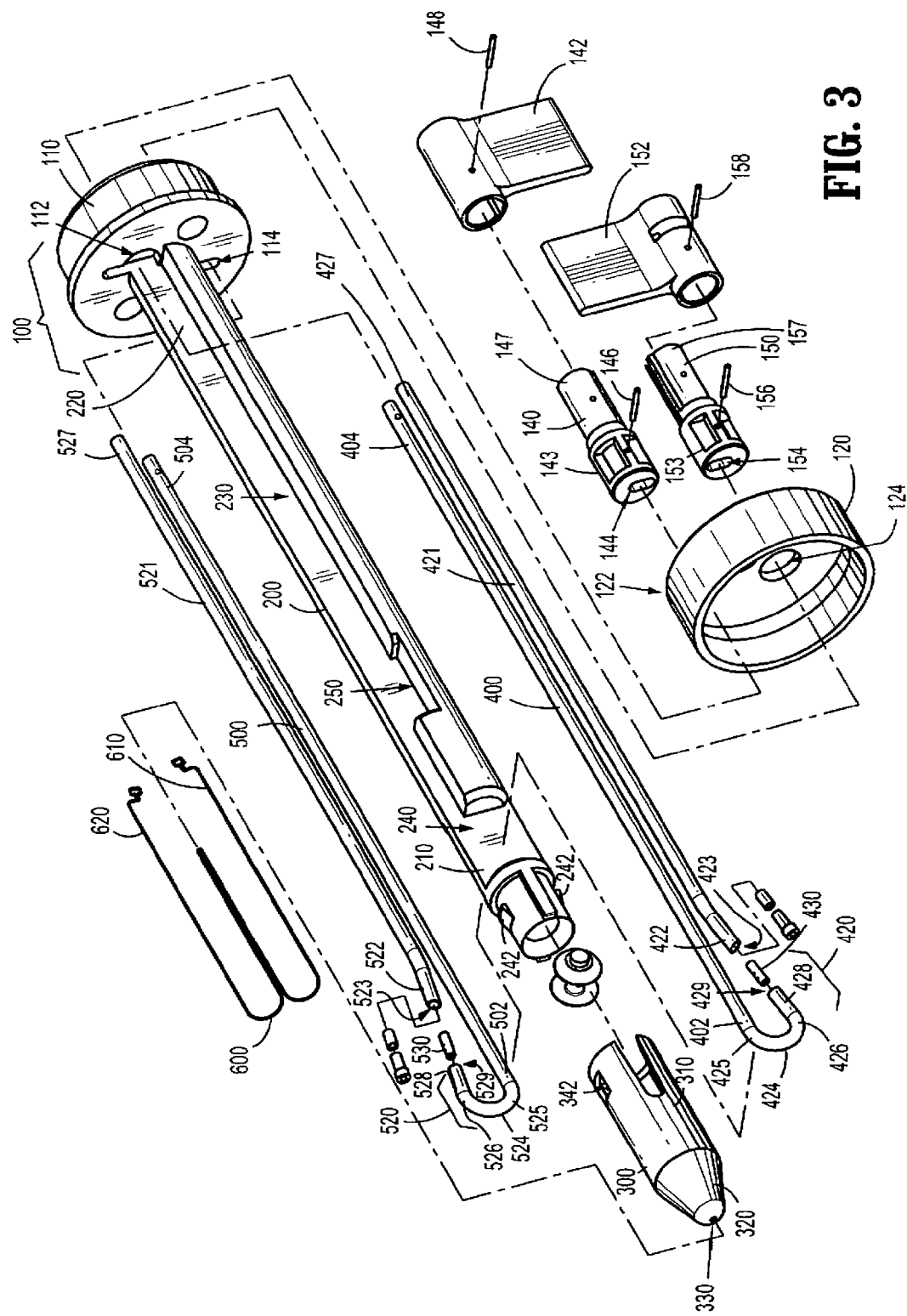
FIG. 3 is an exploded view of the suturing device of FIG. 1 with parts separated.

In the figures and in the description that follows, in which like reference numerals identify similar or identical elements, the term "proximal" will refer to the end of the apparatus which is closest to the operator during use, while the term "distal" will refer to the end which is farthest from the operator, as is traditional.

Figure 4:
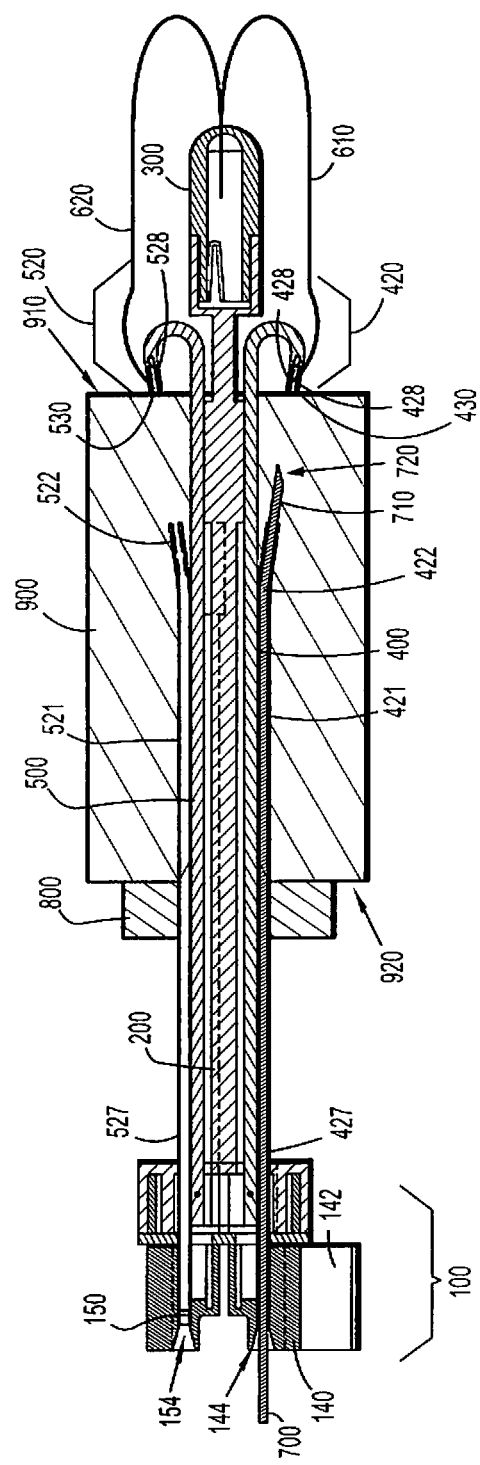
FIG. 4 is a side, cross-sectional view of the suturing instrument of FIG. 1.

Turning now to FIGS. 1-2, suturing instrument 10 defines longitudinal axis "A" and generally includes a housing 100, an elongated tubular member 200 extending distally from the housing 100, a head assembly 300 disposed at a distal end 210 of the elongated tubular member 200, and a pair of arm members 400, 500 positioned about elongated tubular member 200 and extending along elongated tubular member 200. As shown in FIGS. 1-2, two arm members 400, 500 are provided, each having a proximal end 404, 504 and a distal end 402, 502, respectively. However it is envisioned that fewer or more arm members may be provided for use with suturing instrument 10. Arm members 400, 500 are fully disposed within elongated channels 230 and 235 defined on opposing sides of elongated tubular member 200. Each arm member 400, 500 includes a ferrule assembly 420, 520, respectively, disposed at a respective distal end 402, 502, thereof. As will be described in greater detail below, arm members 400 and 500 are selectively rotatable to rotate ferrule assemblies 420 and 520, respectively, between a first position and a second position. Ferrule assembly 420, which is attached to a distal end 402 of arm 400, is rotatable from a first position, wherein ferrule assembly 420 is fully disposed within recess 240 defined within elongated tubular member 200 (FIG. 1), to a second position, wherein ferrule assembly 420 is rotated to extend radially outwardly from recess 240 of elongated tubular member 200 (FIG. 4). Similarly, ferrule assembly 520, which is attached to a distal end 502 of arm member 500, is initially disposed within recess 245 defined within elongated tubular member 200, i.e., the first position (FIG. 1). When rotated to the second position (FIG. 4), ferrule assembly 520 extends radially outwardly from recess 245 of elongated tubular member 200.

With reference now to FIGS. 1-3, each ferrule assembly 420, 520 includes a curved portion 424, 524 and a ferrule holder 428, 528. The curved portions 424, 524 are fixedly attached at respective first ends 425, 525 thereof to the distal ends 402, 502, respectively, of the corresponding arm member 400, 500 and at a second ends 426, 526 thereof to the respective ferrule holders 428, 528 of the respective ferrule assemblies 420, 520. Each ferrule holder 428, 528 includes a lumen 429, 529 for releasably housing a ferrule 430, 530 therein. As can be appreciated, as arm members 400, 500 are rotated, ferrule assemblies 420, 520 are rotated between a first position, in which ferrule holders 428, 528 are fully disposed within recesses 240, 245 of elongated tubular member 200, and a second position, in which ferrule holders 428, 528 extend at least partially radially outwardly from recesses 240, 245 of elongated tubular member 200.

With continued reference to FIGS. 1-3, a guide tube 421, 521, having a respective guide lumen 423, 523 extending therethrough is positioned adjacent each of the arm members 400, 500. Guide tube 421 is positioned in a side-by-side relationship with arm member 400 such that a substantial portion of guide tube 421 and arm 400 run substantially parallel to one another. Similarly, a substantial portion of guide tube 521 runs substantially parallel to arm member 500. As will be discussed in detail below, arm member 400 and guide tube 421 are coupled to one another and are configured to rotate simultaneously with respect to one another such that guide tube 421 rotates about arm member 400 as arm member is rotated between the first and second positions. Similarly, arm member 500 and guide tube 521 are coupled to one another and are configured to rotate simultaneously such that guide tube 521 rotates about arm member 500 as arm member 500 is rotated between the first and second positions.

Guide tubes 421, 521 each include a deflected distal end 422, 522, respectively. The deflected distal ends 422, 522 of guide tubes 421, 521, respectively, are initially positioned within recesses 250 and 255 of elongated tubular member 200 (the first position) but are rotatable to extend radially outwardly from recesses 250 and 255 (the second position) upon rotation of arm member 400, 500, respectively. As mentioned above, the rotation of arm members 400, 500 causes rotation of guide tubes 421, 521 about the respective arm member 400, 500 and also causes simultaneous rotation of ferrule assemblies 420, 520. Thus, the deflected distal ends 422, 522 of guide tubes 421, 521 are rotatable in conjunction with the rotation of ferrule assemblies 420, 520, the importance of which will become more apparent below.

Referring now to FIG. 3, head assembly 300 includes a base portion 310 and a tip portion 320. Tip portion 320 of head assembly 300 may be generally conically shaped to facilitate the insertion of suturing instrument 10 through an opening in tissue 900 (FIG. 4) and/or may also include a blunt tip portion to help avoid damaging tissue upon insertion of instrument 10 into an opening in tissue 900 (FIG. 4). Aperture 330 is configured to releasably retain a portion of suture 600 therein. A first end 610 of suture 600 extends from aperture 330 and is attached to ferrule 430, while a second end 620 of suture 600 extends from aperture 330 and is attached to ferrule 530. Head assembly 300 may be mounted to distal end 210 of elongated tubular member 200 via adhesion, friction-fitting, snap-fitting, or the like. As shown in FIG. 3, head assembly 300 includes notches 342 for engagement with tabs 242 respectively, of elongated tubular member 200 to engage head assembly 300 thereon in a snap-fit engagement.

With continued reference to FIG. 3, housing 100 is positioned at a proximal end 220 of elongated tubular member 200 and generally includes a base 110 and a cover 120. The base 110 and cover 120 are configured to engage one another to form housing 100. Base 110 is engaged with proximal end 220 of elongated tubular member 200 and includes a pair of diametrically opposed apertures 112 and 114, respectively, extending therethrough. Cover 120 similarly includes a pair of opposed apertures 122 and 124. Upon engagement of the base 110 and cover 120 to form housing 100, apertures 112 and 114 of base 110 are aligned with apertures 122 and 124, respectively, of cover 120. A post 140 is positioned through housing 100 via apertures 112 and 122, which are of sufficient diameter to allow post 140 to be rotatable within apertures 112 and 122. A double lumen 144 is defined within distal end 143 of post 140, which extends through housing 100. Double lumen 144 is configured to engage proximal ends 404 and 427 of arm member 400 and guide tube 421, respectively, therein. A pin 146 is inserted through post 140 and arm member 400, to fixedly engage arm member 400 and guide tube 421 within double lumen 144 of post 140, as shown in FIG. 3. Accordingly, the rotation of post 140 causes the like rotation of both arm member 400 and guide tube 421, i.e., the rotation of post 140 rotates arm member 400 between the first and second positions. A proximal end 147 of post 140 extends proximally through aperture 122 of cover 120 and is engaged via pin 148 to flange 142 such that rotation of flange 142 rotates post 140, which in turn rotates arm member 400 and guide tube 421. Flange 142 (and flange 152, described below) provides an ergonomically-friendly surface to grasp and/or push for rotating arm member 400 between the first and second positions.

A second post 150 is inserted through aperture 114 of base 110 and aperture 124 of cover 120 of housing 100. Distal end 153 of post 150 extends through housing 100 and is engaged in a fixed relationship with arm member 500 and guide tube 521 disposed through double lumen 154 and held in place via pin 156. Proximal end 157 of post 150 extends proximally from housing 100 and is engaged with flange 152 via pin 158. Much like the configuration of post 140 and flange 142, rotation of flange 152 rotates post 150, which in turn rotates arm member 500 and guide tube 521, e.g., between the first and second positions. Although not explicitly shown in the drawings, double lumens 144 and 154 of posts 140 and 150, respectively, extend proximally through posts 140 and 150, such that lumen 144 provides a passage extending from the proximal end of housing 100 to the proximal end 427 of guide tube 421 and such that lumen 154 provides a passage extending from the proximal end of housing 100 to the proximal end 527 of guide tube 521. As will become apparent below, these passages allow a user to insert a needle 700 (FIG. 4) through the proximal end of housing 100 into the guide tubes 421, 521.

As shown in FIG. 4, suturing instrument 10 may also include a tissue clamp 800. Tissue clamp 800 is disposed about elongated tubular member 200 and is axially translatable with respect to elongated tubular member 200 along longitudinal axis "A" (FIG. 1). As will become more apparent below, tissue clamp 800 is configured to translate along elongated tubular member 200 to hold tissue 900 in place during suturing. Thus, tissue clamp 800 allows suturing instrument 10 to be used for suturing tissues having varying widths. Further, tissue clamp 800 helps prevent slippage of tissue 900 during suturing, thereby helping to ensure proper placement of the suture(s) 600.

The operation of suturing instrument 10 will now be described with reference to FIGS. 1-4. Initially, flanges 140 and 150 are rotated to the first, or closed position, as shown in FIG. 1, such that ferrule assemblies 420, 520 are fully disposed within recesses 240, 245, respectively, and such that guide tubes 421, 521 are fully disposed within recesses 250, 255, respectively, of elongated tubular member 200. From this closed position, suturing instrument 10 may be inserted into an opening in tissue 900, lead by head assembly 300. Suturing instrument 10 is translated distally through the opening in tissue 900 until the ferrule holders 428, 528, and thus the ferrules 430, 530, are positioned adjacent an internal face 910 of tissue 900. Flange 142 and/or flange 152 are then rotated outwardly, to the position shown in FIG. 4 (the open position), such that ferrule assemblies 420, 520 and guide tubes 421, 521 extend radially outwardly from recesses 240, 245 and 250, 255, respectively, of elongated tubular member 200. At this point, ferrule holders 428, 528 are abutting an internal face 910 of tissue 900, as shown in FIG. 4. Tissue clamp 800 is then moved distally along elongated tubular member 200 to abut external face 920 of tissue 900, thereby holding tissue 900 in place between ferrule holders 428, 528 and tissue clamp 800.

Next, a needle 700 is inserted through aperture 144 of post 140 and into guide tube 421. Upon further distal translation of needle 700 through guide tube 421, distal tip 710 of needle 700 eventually translates completely through guide tube 421, entering tissue 900. Deflected distal tip 422 of guide tube 421 guides needle 700 through tissue 900 in the direction of ferrule holder 428. As needle 700 is urged further distally, needle 700 enters ferrule holder 428, surrounding ferrule 430 such that ferrule 430 is disposed through lumen 720 of needle 700. Lumen 720 may have a slightly smaller diameter than ferrule 430 such that when needle 700 is urged around ferrule 430, ferrule 430 becomes lodged within lumen 720, fixedly retaining ferrule 430 therein via a male-female friction-fit engagement. Alternatively, lumen 720 may taper proximally from distal tip 710 from a first diameter which is larger than the diameter of ferrule 430 to a second diameter which is smaller than the diameter of ferrule 430. In this configuration, further urging of needle 700 around ferrule 430 engages ferrule 430 within lumen 720 in a male-female friction-fit engagement. In another alternative embodiment, needle 700 may be of a sufficiently small diameter to engage a lumen (not shown) defined in ferrule 430. In this embodiment, needle 700 may be urged into the lumen defined in ferrule 430 such that the ferrule 430 and needle 700 are engaged in a male-female friction-fit engagement.

Once ferrule 430 is fixedly engaged with needle 700, as described above, needle 700 may be translated proximally out of ferrule holder 428 and back through tissue 900, with ferrule 430 retained thereon. Since end 610 of suture 600 is attached to ferrule 430, a portion of suture 600 is pulled through tissue 900 along with needle 700 and ferrule 430 such that suture 600 is disposed through tissue 900. Upon further proximal translation of needle 700, needle 700 is removed from guide tube 421 and aperture 144 of post 140. At this point, a middle portion of suture 600 is retained within aperture 330 of head assembly 300, end 610 of suture 600 extends from aperture 300 proximally through tissue 900 due to its engagement with ferrule 430, and end 620 of suture 600 remains attached to ferrule 530, disposed on an internal side 910 of tissue 900 within ferrule holder 528.

Next, needle 700, or a different needle substantially similar to needle 700, is inserted into aperture 154 of post 150 and through guide tube 521. Deflected distal end 522 of guide tube 521 directs needle 700 through tissue 900 and toward ferrule holder 528. As similarly described above, needle 700 is then advanced through ferrule holder 528 to engage ferrule 530 therein in a male-female friction-fit engagement (or other suitable engagement). Needle 700 and ferrule 530 are then translated proximally back through tissue 900, as described above, such that end 620 of suture 600 is disposed through tissue 900. Needle 700 may then be removed from guide tube 521 and post 150. Once the suture ends 610 and 620 are in place, as described above, tissue clamp 800 may be translated proximally, disengaging external surface 920 of tissue 900. With needle 700 removed from suturing instrument 10 and tissue clamp 800 released from tissue 900, flanges 142, 152 may be rotated to the closed position such that ferrule assemblies 420 and 520 and guide tubes 421 and 521 are rotated back to the closed position in which ferrule assemblies 420 and 520 are fully disposed within recesses 240 and 245, respectively, of elongated tubular member 200 and wherein deflected distal ends 422, 522 of guide tubes 421, 521, respectively, are fully disposed within recesses 250 and 255, respectively, of elongated tubular member 200.

At this point, the middle portion of suture 600 is retained within aperture 330 of head assembly 300, on an internal side 910 of tissue 900 while ends 610 and 620 of suture 600 extend proximally through tissue 900. From here, instrument 10 may be withdrawn from the opening in tissue 900. As instrument 10 is removed from the opening in tissue 900, the portion of suture 600 is released from aperture 330, such that the portion of suture 600 remains on an internal side 910 of tissue 900. Once instrument 10 is removed, ends 610 and 620, disposed on the external side 920 of tissue 900, may be pulled tight to bring opposing side of the opening toward one another. The suture may then be tied off close the opening in tissue 900.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A suturing device, comprising:
   an elongated tubular member defining a first longitudinal axis;
   at least one guide tube positioned adjacent the elongated tubular member, the guide tube defining a distal end;
   at least one arm member coupled to the elongated tubular member and the guide tube, the at least one arm member including a suture-retaining portion configured to releasably retain a portion of a suture towards a distal end of the elongated tubular member, the at least one arm member and the guide tube configured to rotate in conjunction with one another and relative to the elongated tubular member about a second longitudinal axis that is parallel to the first longitudinal axis between a first position, wherein the suture-retaining portion and the distal end of the guide tube are disposed in close proximity to the elongated tubular member to define a low profile configuration, and a second position, wherein the suture-retaining portion and the distal end of the guide tube extend radially outwardly from the elongated tubular member and are oriented relative to one another to direct a needle inserted through the guide tube towards the suture-retaining portion; and
   a tissue stop slidably disposed about the elongated tubular member and positioned proximally of the suture-retaining portion of the at least one arm member, the tissue stop slidable about the elongated tubular member between a proximal position, wherein the tissue stop is spaced-apart from the suture-retaining portion of the at least one arm member, and a distal position, wherein the tissue stop is approximated relative to the suture-retaining portion of the at least one arm member to hold tissue between the tissue stop and the suture-retaining portion of the at least one arm member.

2. The suturing device according to claim 1, further comprising an actuator disposed at a proximal end of the elongated tubular member, the actuator selectively actuatable to rotate the at least one arm member and the guide tube between the first and second positions.

3. The suturing device according to claim 1, further comprising first and second arm members disposed on opposing sides of the elongated tubular member.

4. The suturing device according to claim 3, further comprising first and second guide tubes disposed on opposing sides of the elongated tubular member.

5. The suturing device according to claim 1, wherein the tissue stop is slidably disposed about the guide tube.

6. A suturing device, comprising:
   an elongated tubular member defining a first longitudinal axis;
   first and second guide tubes positioned adjacent the elongated tubular member on opposed sides of the elongated tubular member, each guide tube defining a distal end;
   a head assembly disposed at a distal end of the elongated tubular member and configured to receive a portion of a suture;
   first and second arm members coupled to the elongated tubular member on opposed sides of the elongated tubular member and to the respective first and second guide tubes, each of the first and second arm members including a suture-retaining portion configured to releasably retain a portion of the suture towards a distal end of the elongated tubular member, the first arm member and first guide tube configured to rotate in conjunction with one another and relative to the elongated tubular member about a second longitudinal axis that is parallel to the first longitudinal axis between a first position, wherein the suture-retaining portion of the first arm member and the distal end of the first guide tube are disposed in close proximity to the elongated tubular member to define a low profile configuration, and a second position, wherein the suture-retaining portion of the first arm member and the distal end of the first guide tube extend radially outwardly from the elongated tubular member and are oriented relative to one another to direct a needle inserted through the first guide tube towards the suture-retaining portion of the first arm member; and
   a tissue stop slidably disposed about the elongated tubular member, the tissue stop slidable about the elongated tubular member between a proximal position, wherein the tissue stop is spaced-apart from the suture-retaining portions of the first and second arm members, and a distal position, wherein the tissue stop is approximated relative to the suture-retaining portions of the first and second arm members, wherein, with the first and second arm members disposed in the second position and the tissue stop disposed in the approximated position, the tissue stop and the first and second arm members are configured to cooperate to hold tissue therebetween.

7. The suturing device according to claim 6, further comprising a first actuator disposed at a proximal end of the elongated tubular member, the first actuator selectively actuatable to rotate the first arm member and the first guide tube the first and second positions.

8. The suturing device according to claim 6, wherein the second arm member and the second guide tube are configured to rotate in conjunction with one another and relative to the elongated tubular member about a third longitudinal axis that is parallel to the first and second longitudinal axes between a first position, wherein the suture-retaining portion of the second arm member and the distal end of the second guide tube are disposed in close proximity to the elongated tubular member to define a low profile configuration, and a second position, wherein the suture-retaining portion of the second arm member and the distal end of the second guide tube extend radially outwardly from the elongated tubular member and are oriented relative to one another to direct a needle inserted through the second guide tube towards the suture-retaining portion of the second arm member.

9. The suturing device according to claim 8, further comprising a second actuator disposed at a proximal end of the elongated tubular member, the second actuator selectively actuatable to rotate the second arm member and the second guide tube between the first and second positions.

10. The suturing device according to claim 8, wherein the first arm member and the first guide tube and the second arm member and the second guide tube are movable independent of one another between their respective first and second positions.

* * * * *